United States Patent
Hong et al.

(10) Patent No.: US 6,749,629 B1
(45) Date of Patent: Jun. 15, 2004

(54) STENT PATTERN WITH FIGURE-EIGHTS

(75) Inventors: James Hong, San Jose, CA (US); E Tina Cheng, Union City, CA (US); Stephen D. Ainsworth, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/892,889

(22) Filed: Jun. 27, 2001

(51) Int. Cl.$^7$ .................................................. A61F 2/06
(52) U.S. Cl. ........................................................ 623/1.15
(58) Field of Search ............................... 623/1.15, 1.16, 623/1.17, 1.2; 606/198

(56) References Cited

U.S. PATENT DOCUMENTS

| | | |
|---|---|---|
| 4,580,568 A | 4/1986 | Gianturco |
| 4,827,321 A | 5/1989 | Baliga |
| 5,102,417 A | 4/1992 | Palmaz |
| 5,104,404 A | 4/1992 | Wolff |
| 5,292,331 A | 3/1994 | Boneau |
| 5,449,373 A | 9/1995 | Pinchasik et al. |
| 5,607,442 A | 3/1997 | Fischell et al. |
| 5,632,771 A | 5/1997 | Boatman et al. |
| 5,643,312 A | 7/1997 | Fischell et al. |
| 5,669,932 A | 9/1997 | Fischell et al. |
| 5,674,241 A | 10/1997 | Bley et al. |
| 5,674,278 A | 10/1997 | Boneau |
| 5,697,971 A | 12/1997 | Fischell et al. |
| 5,733,303 A | 3/1998 | Israel et al. |
| 5,741,327 A | 4/1998 | Frantzen |
| 5,755,781 A | 5/1998 | Jayaraman |
| 5,776,161 A | 7/1998 | Globerman |
| 5,807,404 A | 9/1998 | Richter |
| 5,810,872 A | 9/1998 | Kanesaka et al. |
| 5,824,040 A | 10/1998 | Cox et al. |
| 5,836,964 A | 11/1998 | Richter et al. |
| 5,843,120 A | 12/1998 | Israel et al. |
| 5,843,168 A | 12/1998 | Dang |
| 5,843,175 A | 12/1998 | Frantzen |
| 5,853,419 A | 12/1998 | Imran |

(List continued on next page.)

FOREIGN PATENT DOCUMENTS

| | | |
|---|---|---|
| DE | 297 08879 U1 | 9/1997 |
| EP | 0 088 093 B1 | 1/1986 |
| EP | 0 372 789 A3 | 6/1990 |
| EP | 0 806 190 A1 | 11/1997 |
| EP | 0 888 757 A1 | 1/1999 |
| WO | WO 95/03010 | 2/1995 |
| WO | WO 97/32544 | 9/1997 |
| WO | WO 98/22159 | 5/1998 |
| WO | WO 99/17680 | 4/1999 |
| WO | WO 99/62430 | 12/1999 |
| WO | WO 00/42945 | 7/2000 |
| WO | WO 00/42946 | 7/2000 |
| WO | WO 00/62710 | 10/2000 |

OTHER PUBLICATIONS

Application for U.S. Letter patent Ser. No. 09/343,962 filed Jun. 20, 1999.

*Primary Examiner*—Corrine McDermott
*Assistant Examiner*—William Matthews
(74) *Attorney, Agent, or Firm*—Fulwider Patton Lee & Utecht, LLP

(57) ABSTRACT

The invention is directed to an expandable stent for implanting in a body lumen, such as a coronary artery, peripheral artery, or other body lumen. The invention provides for an intravascular stent having a plurality of cylindrical rings connected by links. The rings have peaks and valleys from which extend straight and nonlinear bar arms, forming a figure-eight. The links connecting the cylindrical rings may be straight, undulating, or include bounded apertures for additional flexibility.

13 Claims, 7 Drawing Sheets

U.S. PATENT DOCUMENTS

| | | |
|---|---|---|
| 5,868,781 A | 2/1999 | Killion |
| 5,868,783 A | 2/1999 | Tower |
| 5,876,449 A | 3/1999 | Starck et al. |
| 5,879,370 A | 3/1999 | Fischell et al. |
| 5,879,381 A * | 3/1999 | Moriuchi et al. ........... 606/195 |
| 5,879,382 A | 3/1999 | Boneau |
| 5,893,887 A | 4/1999 | Jayaraman |
| 5,911,754 A | 6/1999 | Kanesaka et al. |
| 5,913,895 A | 6/1999 | Burpec et al. |
| 5,922,005 A | 7/1999 | Richter et al. |
| 5,922,020 A | 7/1999 | Klein et al. |
| 5,925,061 A | 7/1999 | Ogi et al. |
| 5,931,866 A | 8/1999 | Frantzen |
| 5,935,162 A | 8/1999 | Dang |
| 5,938,682 A | 8/1999 | Hojeibane et al. |
| 5,938,697 A | 8/1999 | Killion et al. |
| 5,948,016 A | 9/1999 | Jang |
| 5,954,743 A | 9/1999 | Jang |
| 5,964,798 A | 10/1999 | Imran |
| 5,967,986 A | 10/1999 | Cimochowski et al. |
| 5,968,093 A | 10/1999 | Kranz |
| 5,972,018 A | 10/1999 | Israel et al. |
| 5,980,552 A | 11/1999 | Pinchasik et al. |
| 5,993,489 A | 11/1999 | Lewis et al. |
| 6,001,125 A | 12/1999 | Golds et al. |
| 6,004,348 A | 12/1999 | Banas et al. |
| 6,013,091 A | 1/2000 | Ley et al. |
| 6,017,365 A | 1/2000 | Von Oepen |
| 6,019,789 A | 2/2000 | Dinh et al. |
| 6,022,371 A | 2/2000 | Killion |
| 6,022,374 A | 2/2000 | Imran |
| 6,033,433 A | 3/2000 | Ehr et al. |
| 6,033,435 A | 3/2000 | Penn et al. |
| 6,039,755 A | 3/2000 | Edwin et al. |
| 6,039,756 A | 3/2000 | Jang |
| 6,042,597 A | 3/2000 | Kveen et al. |
| 6,042,606 A | 3/2000 | Frantzen et al. |
| 6,048,361 A | 4/2000 | Von Oepen |
| 6,051,020 A | 4/2000 | Goicoechea et al. |
| 6,053,940 A | 4/2000 | Wijay |
| 6,053,941 A | 4/2000 | Lindenberg et al. |
| 6,053,943 A | 4/2000 | Edwin et al. |
| 6,056,775 A | 5/2000 | Borghi et al. |
| 6,056,776 A | 5/2000 | Lau et al. |
| 6,059,822 A | 5/2000 | Kanesaka et al. |
| 6,063,113 A | 5/2000 | Kvteladze et al. |
| 6,066,168 A | 5/2000 | Lau et al. |
| 6,066,169 A | 5/2000 | McGuinness |
| 6,068,656 A | 5/2000 | Von Oepen |
| 6,071,298 A | 6/2000 | Lanshinski et al. |
| 6,077,297 A | 6/2000 | Robinson et al. |
| 6,080,191 A | 6/2000 | Summers |
| 6,083,259 A | 7/2000 | Frantzen |
| 6,086,604 A | 7/2000 | Fischell et al. |
| 6,086,611 A | 7/2000 | Duffy et al. |
| 6,090,127 A | 7/2000 | Globerman |
| 6,093,199 A | 7/2000 | Brown et al. |
| 6,093,203 A | 7/2000 | Uflacker |
| 6,099,455 A | 8/2000 | Columbo et al. |
| 6,099,559 A | 8/2000 | Nolting |
| 6,099,560 A | 8/2000 | Penn et al. |
| 6,099,561 A | 8/2000 | Alt |
| 6,102,940 A | 8/2000 | Robichon et al. |
| 6,106,548 A | 8/2000 | Roubin et al. |
| 6,113,627 A | 9/2000 | Jang |
| 6,113,628 A | 9/2000 | Borghi |
| 6,117,165 A | 9/2000 | Becker |
| 6,123,721 A | 9/2000 | Jang |
| 6,129,754 A | 10/2000 | Kanesaka et al. |
| 6,129,755 A | 10/2000 | Mathis et al. |
| 6,152,957 A | 11/2000 | Jang |
| 6,156,052 A | 12/2000 | Richter et al. |
| 6,162,243 A | 12/2000 | Gray et al. |
| 6,179,868 B1 | 1/2001 | Burpee et al. |
| 6,183,506 B1 | 2/2001 | Penn et al. |
| 6,187,034 B1 | 2/2001 | Frantzen |
| 6,190,403 B1 | 2/2001 | Fischell et al. |
| 6,200,334 B1 | 3/2001 | Jang |
| 6,206,916 B1 | 3/2001 | Furst |
| 6,217,608 B1 | 4/2001 | Penn et al. |
| 6,241,762 B1 | 6/2001 | Shanley |
| 6,258,116 B1 | 7/2001 | Hojeibane |
| 6,264,685 B1 * | 7/2001 | Ahari ....................... 623/1.15 |

* cited by examiner

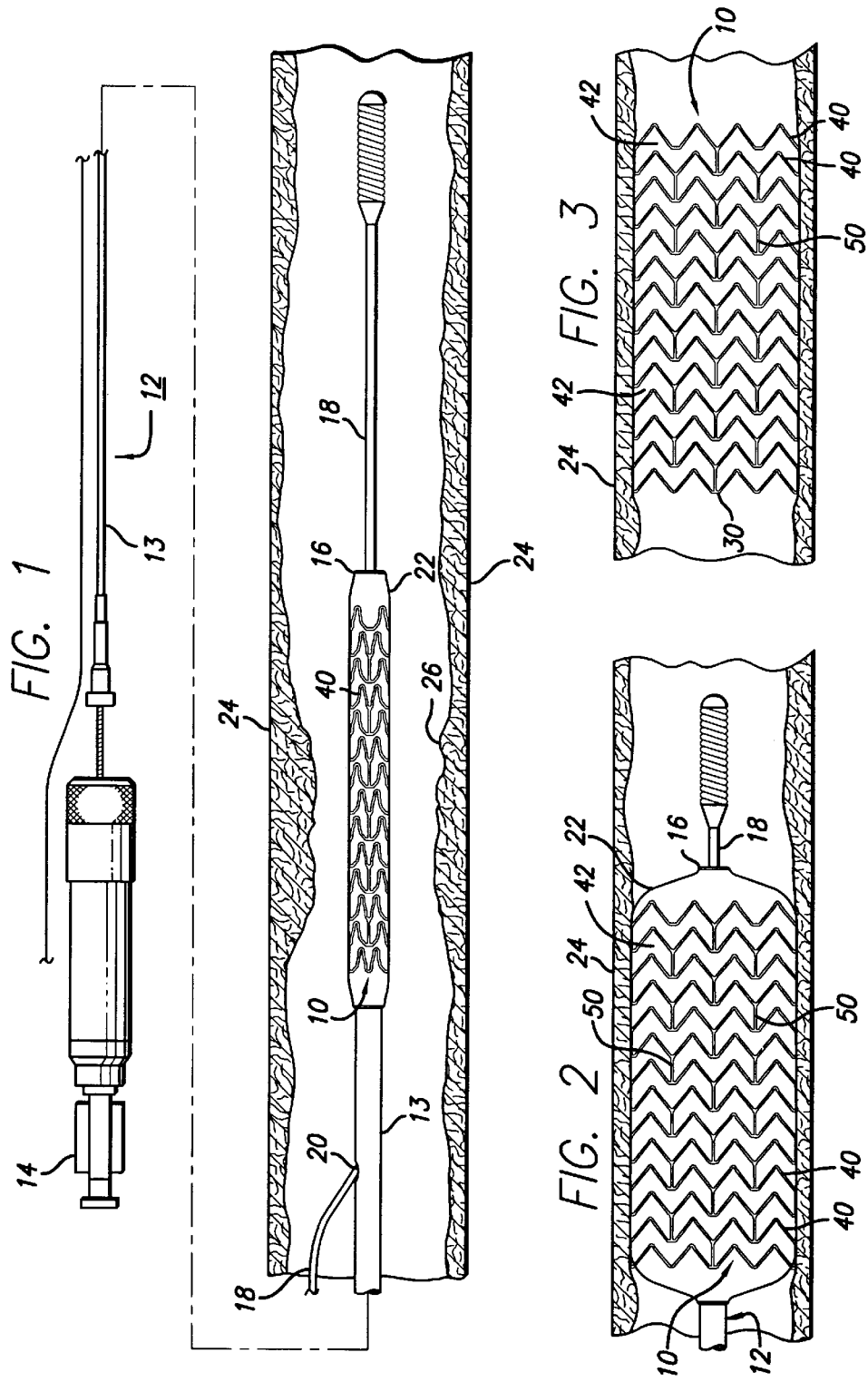

STENT PATTERN WITH FIGURE-EIGHTS

BACKGROUND OF THE INVENTION

This invention relates to endoluminal prostheses such as vascular repair devices, and in particular intravascular stents, which are adapted to be implanted into a patient's body lumen, such as a blood vessel or coronary artery, to maintain the lumen's patency. Stents are particularly useful in the treatment of atherosclerotic stenosis and are most frequently used in connection with coronary angioplasty.

Stents are tubular, usually cylindrical devices which hold open a segment of blood vessel or other body lumen. They also are suitable to support and hold back a dissected arterial lining that can occlude the lumen. At present, numerous models of stents are marketed throughout the world. While some of these stents are flexible and have the appropriate strength and rigidity needed to hold open a lumen such as a coronary artery, each stent design typically represents a compromise between the stent's flexibility and its radial strength. What has been needed, and heretofore unavailable, is a stent which has a high degree of flexibility so that it can be advanced through tortuous lumen and readily expanded, and yet have the mechanical strength to hold open the lumen or artery into which it is implanted and provide adequate vessel wall coverage.

At least some in the stent industry also perceive a problem with "fishscaling." Fishscaling, describes the twisting or bending of stent struts, which results in the struts not conforming to a generally cylindrical plane around the circumference of the stent. Fishscaling can result from the manufacturing process, as in the case of the Medinol, Ltd. NIR® stent. Fishscaling also can occur during the stent placement process, such as when portions of the stent surface are forced outward as the stent bends while advancing through tortuous lumen. Some in the stent art believe that fishscaling can damage the blood vessel through which the stent is being advanced. Therefore, there is a perceived need for a stent that reduces or eliminates fishscaling.

SUMMARY OF THE INVENTION

The present invention is directed to an endoluminal prosthesis, such as an intravascular stent, which is highly flexible along its longitudinal axis to facilitate delivery through tortuous body lumens, but which is strong and stable enough radially in its expanded condition to maintain the patency of a body lumen when the stent is implanted therein. The stent also reduces fishscaling.

The stent of the present invention includes a plurality of generally cylindrical elements, also known as rings, that are interconnected to form the stent. The stent typically is mounted on a balloon catheter if it is balloon expandable, or else it can be mounted on a catheter without a balloon if it is self-expanding.

Each of the cylindrical rings or elements has a proximal end and a distal end and a cylindrical plane defined by a cylindrical outer wall surface that extends circumferentially between the proximal end and the distal end of the cylindrical ring. In the preferred embodiment, cylindrical rings are interconnected by three links which attach one cylindrical ring to an adjacent cylindrical ring. The links are positioned substantially within the cylindrical plane of the outer wall surface of the cylindrical rings. The design of these highly flexible, interconnected members provides for uniform scaffolding and a high percentage of vessel wall coverage.

The cylindrical rings typically are formed of a plurality of peaks and valleys. A straight strut, also called a bar arm, and a curved, or nonlinear bar arm extend from each peak or valley. In several preferred embodiments, this arrangement gives each ring the appearance of a series of figure-eights. In this configuration, at least one link attaches each cylindrical ring to an adjacent cylindrical ring. In the preferred embodiments, each cylindrical ring has six peaks and valleys and three to six connecting links. The cylindrical rings and flexible links are preferably not separate structures, although they have been conveniently referred to separately for ease of identification.

Typically, a balloon expandable stent is made from a stainless steel alloy or similar material. The cylindrical rings of the stent are plastically deformed when expanded by the balloon.

The links may take various configurations. One such configuration is a straight link. Another is an undulating or serpentine shape, which makes the links more flexible. The undulating links can include bends connected by straight portions, wherein the substantially straight portions are perpendicular to the stent's longitudinal axis. Another configuration places one or more apertures, such as an oval, rectangle, or dog bone shape, in a straight link. The apertures are typically longer in one direction than another, with the longer direction oriented preferably perpendicular to the longitudinal axis of the stent. These links are described in two United States patent applications by Ainsworth and Cheng, Ser. No. 09/746,746, filed Dec. 22, 2000, and assigned to Advanced Cardiovascular Systems, Inc., Santa Clara, Calif. (ACS) the assignee of the present application, and of Ser. No. 09/564,151, filed May 3, 2000, also assigned to ACS. The entire earlier applications are incorporated herein by reference.

In the case of the undulating links that interconnect the cylindrical rings, the positioning of the unexpanded links also enhances the flexibility by allowing uniform flexibility when the stent is bent in any direction along its longitudinal axis. The cylindrical rings of the stent can expand radially outwardly without a balloon when the stent is formed from a superelastic alloy, such as nickel titanium (NiTi) alloys. These so-called "self-expanding" stents expand upon application of a temperature change or when a stress is relieved, as in the case of a pseudo-elastic phase change.

The number of peaks, valleys, links, and cylindrical rings can be varied as the application requires. When using flexible links, the link typically does not expand when the cylindrical rings of the stent expand radially outwardly, but the links do continue to provide flexibility and to also provide a scaffolding function to assist in holding open the artery. Each flexible link is configured so that it promotes flexibility.

The configuration of the rings provides the stent with a high degree of flexibility along the stent axis, and reduces the tendency of stent fishscaling. Further, because the links do not expand or stretch when the stent is radially expanded, the overall length of the stent is substantially the same in the unexpanded and expanded configurations. In other words, the stent will not appreciably shorten upon expansion.

Other embodiments of the invention also include figure-eight type rings with a linear and non-linear bar arm. Ring orientation and link shape vary the features of these other embodiments.

The stent is formed from a tube by laser cutting the pattern of cylindrical rings and flexible links in the tube. The stent also may be formed by laser cutting a flat metal sheet in the pattern of the cylindrical rings and links, and then rolling the pattern into the shape of the tubular stent and providing a longitudinal weld to form the stent.

BRIEF DESCRIPTION OF THE DRAWINGS

FIG. 1 is an elevation view, partially in section, of a stent which is mounted on a rapid-exchange delivery catheter and positioned within an artery.

FIG. 2 is an elevation view, partially in section, similar to that shown in FIG. 1, wherein the stent is expanded within the artery so that the stent embeds within the arterial wall.

FIG. 3 is an elevation view, partially in section, showing the expanded stent implanted within the artery after withdrawal of the rapid-exchange delivery catheter.

DETAILED DESCRIPTION OF THE PREFERRED EMBODIMENTS

Figure 4:
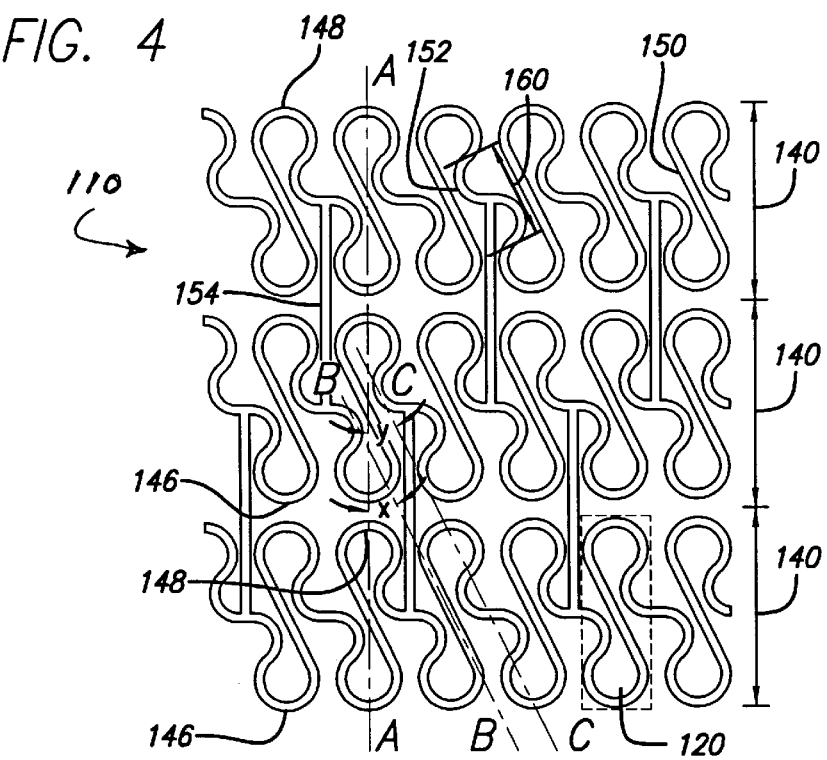
FIG. 4 is a flattened plan view of a stent pattern which illustrates a preferred configuration of the present invention.

The present invention improves on existing endovascular prostheses, such as stents, by providing a more flexible device with a uniquely designed ring pattern and novel interconnecting members or links. A significant aspect of the invention is the arrangement of linear and non-linear bar arms, or struts, which in several preferred embodiments form a figure-eight. In addition to providing better longitudinal flexibility, the stent of the present invention also provides good radial strength and a high degree of scaffolding of a vessel wall, such as a coronary artery. The design of the stent struts and the interconnecting members (also called links or connectors, and, by some in the art, struts) and their placements provide for uniform scaffolding and a high degree of vessel wall coverage.

The present invention is the configuration of the material used to make an endoluminal prosthesis such as a stent. In other words, it is the stent pattern. Various embodiments, including the figure-eight patterns 120, 520, 620, 720, are depicted in FIGS. 4 and 12–14, and will be discussed in detail below. Other embodiments, such as those in FIGS. 5–8, will also be explained. First, the general use of stents will be discussed.

FIGS. 1–3 can represent any balloon expandable stent 10 with which the various configurations of the present invention can be used. FIG. 1 depicts a stent 10 with interconnected cylindrical rings 40 mounted on a catheter assembly 12 which is used to deliver the stent 10 and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well-known methods of an over-the-wire system (not shown) or a well-known rapid exchange catheter system, such as the one shown in FIG. 1. The stent 10 in FIGS. 1–3 conceptually represents any type of stent well-known in the art—one comprising a plurality of undulating cylindrical rings 40. An example of such a stent is the Tetra® stent, made by ACS.

Catheter assembly 12 as depicted in FIG. 1 includes an RX port 20 where the guide wire 18 exits the catheter. The distal end of the guide wire 18 exits the catheter distal end 16 so that the catheter advances along the guide wire on a section of the catheter between the RX (rapid exchange) port 20 and the catheter distal end 16. As is known in the art, the guide wire lumen which receives the guide wire is sized for receiving various diameter guide wires to suit a particular application. The stent is mounted on expandable member 22 (e.g., an angioplasty balloon) and is crimped tightly thereon, so that the stent and expandable member present a low profile diameter for delivery through the arteries.

As shown in FIG. 1, a partial cross-section of an artery 24 has a small amount of plaque that has been previously treated by angioplasty or other repair procedure. Stent 10 is used to repair a diseased or damaged arterial wall as shown in FIG. 1, or a dissection, or a flap, all of which are commonly found in the coronary arteries and other blood. The stent 10, and the stent of the present invention, also can be placed and implanted without any prior angioplasty.

In a typical procedure to implant stent 10, the guide wire 18 is advanced through the patient's vascular system by well-known methods, so that the distal end of the guide wire is advanced past the plaque or diseased area 26. Prior to implanting the stent, the cardiologist may wish to perform an angioplasty or other procedure (i.e., atherectomy) in order to open and remodel the vessel and the diseased area. Thereafter, the stent delivery catheter assembly 12 is advanced over the guide wire so that the stent is positioned in the target area. The expandable member or balloon 22 is inflated by well-known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 holds open the artery after the catheter is withdrawn, as illustrated by FIG. 3. In the preferred embodiment, the stent is formed from a cylindrical tube with a constant wall thickness, so that the straight and undulating components of the stent are relatively flat in transverse cross-section, so that when the stent is expanded, its flat surface is pressed into the wall of the artery, and as a result does not interfere with the blood flow through the artery. After the stent is pressed into the wall of the artery, it eventually becomes covered with endothelial cell growth which further minimizes blood flow interference. The undulating portion of the stent provides good tacking characteristics to prevent stent movement within the artery. Because the cylindrical rings 40 are closely spaced at regular intervals, they provide uniform support for the wall of the artery, and consequently are well adapted to tack up and hold in place small flaps or dissections in the wall of the artery, as illustrated in FIGS. 2 and 3.

The stent 10 in FIG. 3 has fourteen cylindrical rings 40. The rings are connected by links 50. For the purpose of the present invention, the cylindrical rings 40 could also be connected by welds in a manner similar to the "S" series of stents presently sold by Medtronic Ave, Inc., or in some other manner.

FIGS. 4–14 depict various configurations and features of the present invention. Turning to FIG. 4, a portion of a stent 110 is shown in a flattened condition so that the pattern can be clearly viewed, even though the preferred embodiment is not made this way. The stent is typically formed from a tubular member, but it can be formed from a flat sheet such as the portion shown in FIG. 4 and rolled into a cylindrical configuration. Although welding flat sheets or rings is not a preferred method of manufacture, it can be used.

FIG. 4 represents three cylindrical rings 140 of stent 110. The stent can have any number of rings, and, depending upon the size of the rings, it is preferred that a stent of the present invention have more than the three rings 140 shown in FIG. 4. For reference, line A—A represents the longitudinal axis of a stent using the pattern depicted in FIG. 4. Each cylindrical ring 140 has a cylindrical ring proximal end 146 and a cylindrical ring distal end 148. The proximal ring ends 146 and distal ring ends 148 can also be considered to form a pattern of peaks and valleys, i.e., an undulating shape. In the embodiment in FIG. 4, the stent axis A—A passes through adjacent peaks and valleys. The ring ends, or peaks and valleys, 146 and 148 are curved. They are connected by a linear bar arm 150 and a nonlinear bar arm 152. Each cylindrical ring 140 is connected by one or more connecting links 154. For reference, line B—B represents the longitudinal axis of linear bar arm 150, while C—C represents the axis of nonlinear bar arm 152. The preferred embodiment of the invention depicted in FIG. 4 shows B—B and C—C parallel to each other. While this is a preferred embodiment, the invention is not so limited. Nonlinear bar arm 152 preferably comprises at least one full, three hundred sixty degree sine wave element 160. The sinusoidal portion 160 can possess more pointed or more rounded peaks and valleys with more linear connections, like a zigzag shape, and the same is true for the peaks and valleys 146 and 148 of the cylindrical rings.

The present invention frequently results in a repeating pattern of figure-eights. In FIG. 4, the figure-eight is made up of a straight bar arm 150 and portions of non-linear bar arms 152. The tops and bottoms of the figure-eight 120 are the peaks 146 and valleys 148 of rings 140. The peaks and valleys are sometimes generically referred to as crests. The selection of which crest is a peak and which crest is a valley is arbitrary and done for ease of reference. Those in the art will understand that, depending upon one's reference, a peak can be a valley, and vice versa. Moreover, those in the art will understand from context the meanings of peak, valley and crest.

Figure 5:
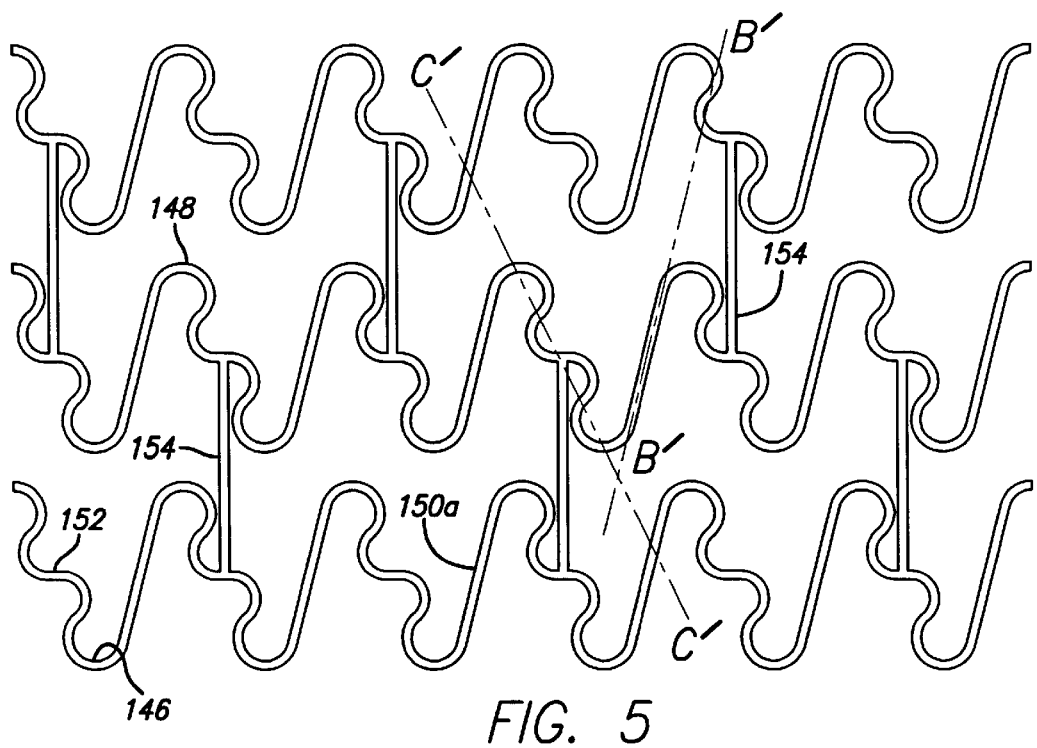
FIG. 5 is a plan view of a variation of the stent pattern shown in FIG. 4.

FIG. 5 represents a modified embodiment of the present invention. Much of the pattern is the same. The principal difference is that in FIG. 5 the axis C'—C' of nonlinear bar arm 152 forms an acute angle with axis B'—B' of linear bar arm 150a. The present invention is intended to cover all configurations in which the angle between the axes of the bar arms 150 and 152 ranges from zero degrees (i.e., the axes are parallel) to more than 90°. This can be understood more fully in the context of FIG. 4. Axes B—B and C—C intersect the longitudinal axis A—A of the stent, forming angles X and Y. Because B—B and C—C are parallel, acute angles X and Y are equal. The relationship between axes B—B and C—C and their corresponding bar arms 150 and 152 can be altered by changing angles X and Y. The change in the angles can be of equal or different magnitude. As those in the art will appreciate, such changes can affect the size and shape of each ring 140 and the flexibility of the stent.

Figure 6:
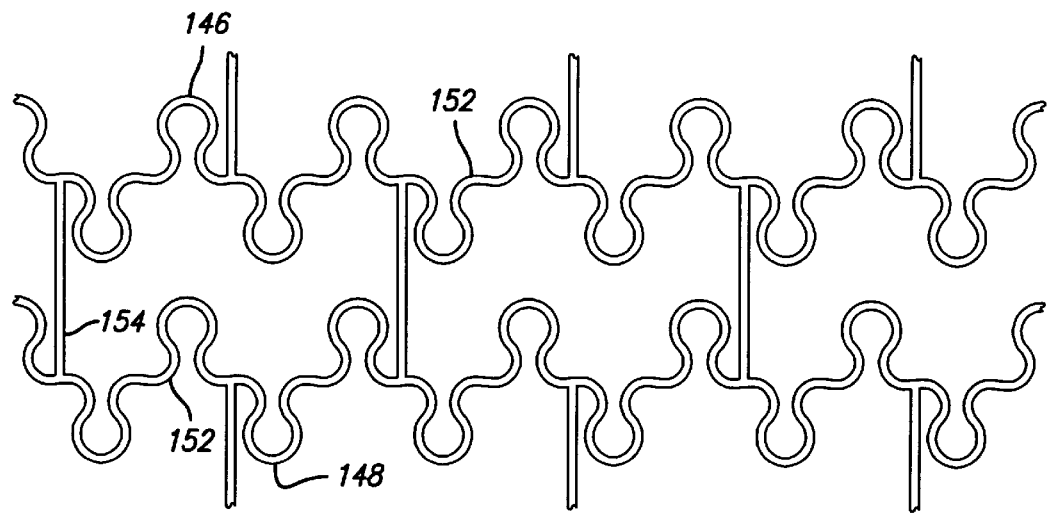
FIG. 6 is a plan view of another variation of the stent pattern shown in FIG. 4.

FIG. 6 is a partial stent pattern that represents another embodiment of the present invention, in which the linear bar arm 150 has been replaced by an additional nonlinear bar arm 152. In other words, all of the bar arms, also known as struts, of the cylindrical rings of the stent comprise sinusoidally shaped or generally undulating structures.

Figure 7:
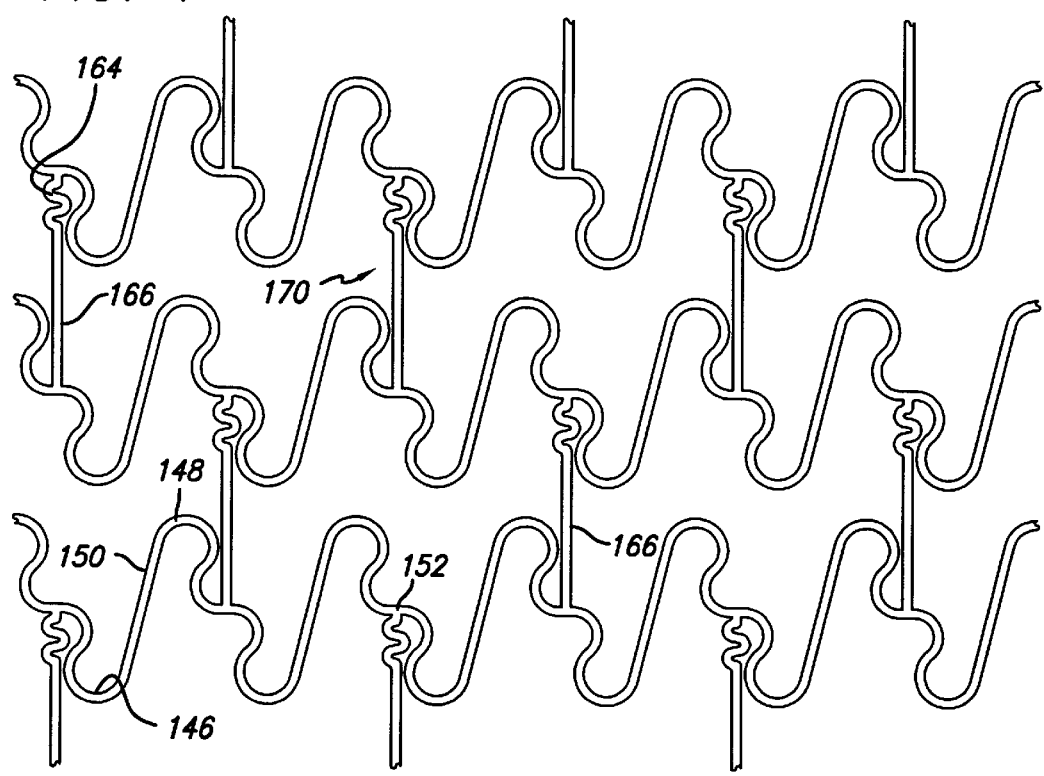
FIG. 7 is a plan view of a variation of the stent pattern in FIG. 4, with an undulating type of flexible connecting link.

FIGS. 7–11 depict more variations of the present invention. In particular they address the flexibility of the stent by increasing the flexibility of the connecting link. This can be accomplished in a number of ways. FIG. 7, for example, depicts a link 170 comprised of a straight portion 166 and an undulating portion 164. The undulating or corrugated links 164 permit the stent to flex more than a straight link along the longitudinal axis, which substantially enhances delivery of the stent to the target site. The size and shape of the undulations can be varied to achieve different degrees of flexibility. This is discussed more in the above-referenced application, Ser. No. 09/746,746, assigned to ACS by Ainsworth and Cheng.

Figure 8:
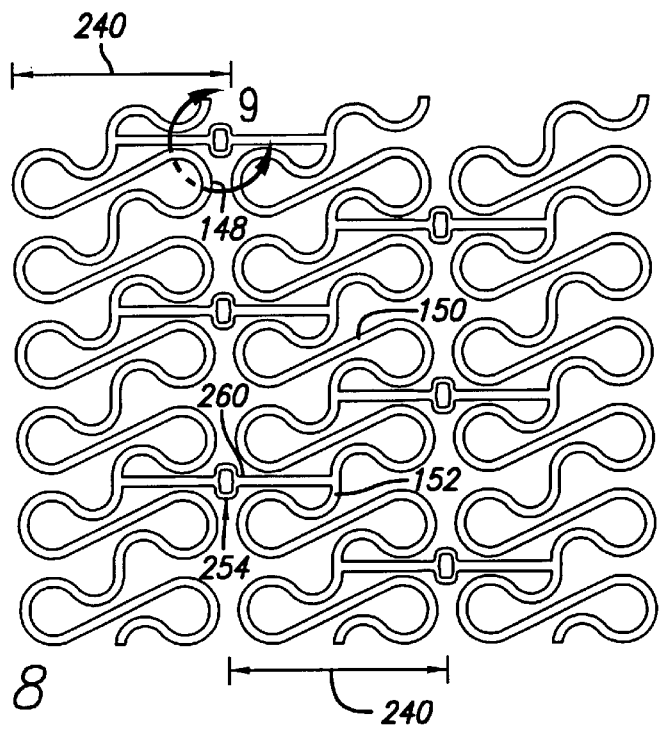
FIG. 8 is a plan view of another embodiment of the stent pattern in FIG. 4, with a rectangular aperture as part of the connecting link.
Figure 9:
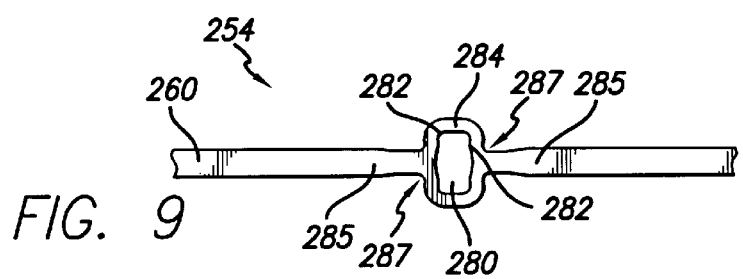
FIG. 9 is a plan view of a single, straight, connecting link with a generally rectangular aperture.

FIGS. 8 and 9 depict another type of link that provides improved stent flexibility in tortuous vessels. A portion of a stent 210 has cylindrical rings 240 connected by links 254. Link 254 has a straight portion 260 that is preferably parallel to the stent's longitudinal axis and a generally rectangular aperture 280 bounded on all sides. Link portions 282 define two sides of rectangular aperture 280 and are generally perpendicular to the stent's longitudinal axis. Link portions 284 connect the link portions 282. Tapered link portions 285 are connected to perpendicular link portions 282 at radii 287.

The increase in stent flexibility created by aperture 280 and the surrounding structure is easily understood. As a stent passes through a curved vessel, half the stent is in tension at the widest part of the curve, and the other half of the stent is in compression, at the narrowest part of the curve. Thus, one half of the stent wants to expand, and the other half wants to contract and the link aperture permits either. As those in the art will appreciate, less force is required to deform the structure bounding aperture 280 than would be necessary to elongate or compress a link if were a straight structure like link portion 260.

Figure 10:
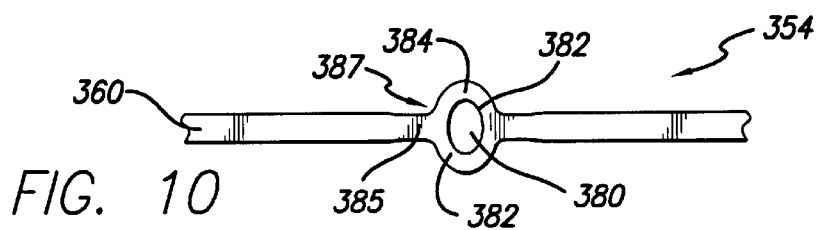
FIG. 10 is a plan view of a single, straight, connecting link with a generally oval aperture.

FIG. 10 is conceptually similar to FIG. 9. Aperture 380 is shaped like an oval or ellipse, with the major axis of the ellipse running perpendicular to the stent's longitudinal axis. In other words, the long part of the ellipse 382 is perpendicular to the stent's longitudinal axis, the short elliptical part 384 is parallel to the longitudinal axis. The link 354 also includes tapered portion 385 and radius portion 387. The structural portion surrounding the elliptical aperture 380 responds to stress in much the same way as the rectangular structure in FIG. 9. As the ellipse is stretched in tension it becomes more circular and less elliptical. As the ellipse is placed in compression, it becomes more elliptical, approaching the shape of a thin rectangle, a slit, or even two separate rounded apertures separated by a contact point.

In the one embodiment of the flexible link with an oval or elliptical aperture, the major and minor axis of an ellipse are parallel and perpendicular to the longitudinal axis of the stent. Thus, in a general sense, the ellipse can be thought of as similar to a rectangle to the extent it has two long sides and two short sides. Preferably, the long sides, i.e., those associated with the major axis of the ellipse, are transverse to the longitudinal axis of the stent.

Figure 11:
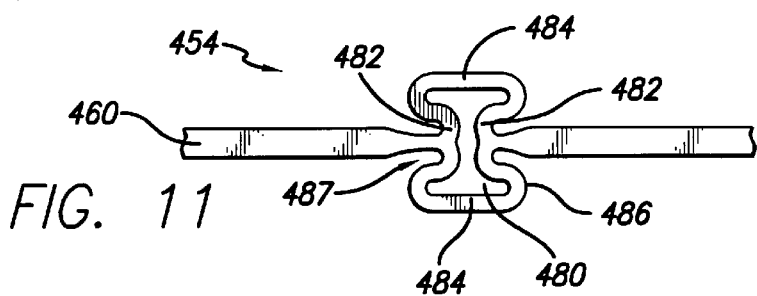
FIG. 11 is a detailed plan view of a single straight connecting link with a generally dog bone-shaped aperture.

FIG. 11 depicts a link 454 with a dumbbell or dog bone shaped aperture 480. Straight portion 460 of link 454 intersects transverse portion 482. The aperture 480 is bounded by transverse and parallel portions 482 and 484 and four curved portions 486. As tension is applied to link 454, radius portions 487 and curved portions 486 tend to straighten as distance between transverse portions 482 increases. When the link 454 is compressed, transverse portions 482 will approach each other to the point of touching.

As one of ordinary skill in the art will appreciate, the flexibility of links 254, 354, and 454 in FIGS. 9–11 can be controlled by the dimensions of various portions of the links, such as tapering straight portions 460 where it meets transverse portion 482. One could also, separately or in combination with the taper, vary radius portion 487 or modify the widths of various structural elements, such as portions 460, 482, 484 or 486. Although perhaps obvious, it should be emphasized that the term straight is used in a relative sense. In other words, straight portion 460 should be considered straight despite the taper depicted in FIG. 11. Similarly, linear bar arm 150 could have a varying width or thickness at different points while still defining a straight line following axis B—B. Common sense, however, means that non-linear bar arm 152 is not straight, despite having a straight axis.

Figure 12:
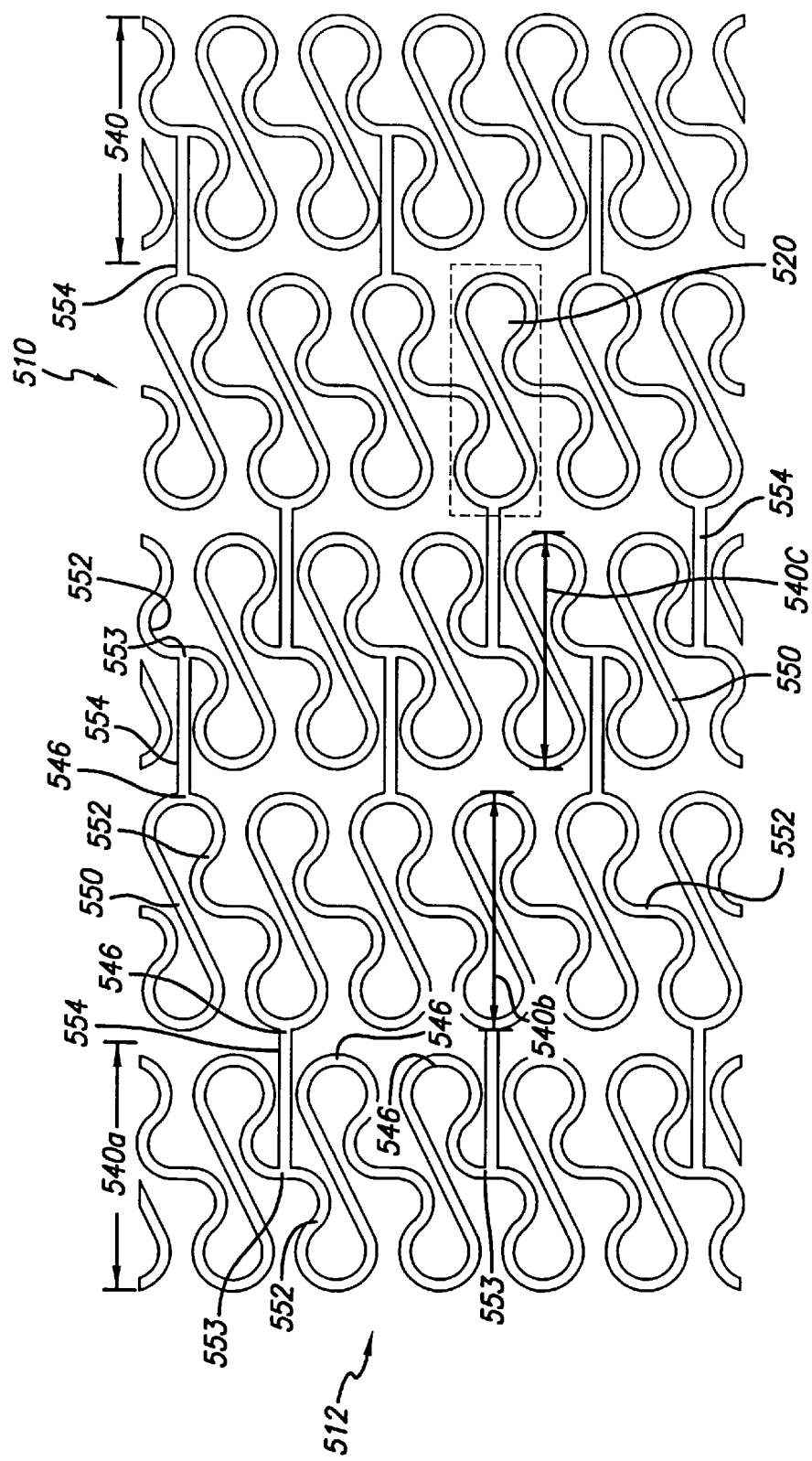
FIG. 12 is a plan view of the stent pattern with the adjacent rings out-of-phase.

FIG. 12 depicts another embodiment of the present invention. This is a 6-crown, 3-link stent pattern 510 with one straight bar arm 550 and one non-linear bar arm 552 that ultimately form a series of figure-eights 520. Each ring 540 is positioned "out-of-phase" relative to its adjacent ring, potentially increasing flexibility relative to an "in-phase" configuration. The preferred stent will comprise more than the rings shown in FIG. 12. Starting from the proximal end 512 of the stent 510, straight links 554 are used, with the proximal end extending from approximately the middle 553 of the non-linear bar arms 552 to the crests 546 in the adjacent ring 540b. In the second ring 540b, there are no linkage connections at the mid-section 553 of the non-linear bar arms 552; instead the links are joined at the peak of the distal crests 546 in the second ring 540b to the mid-section 553 of the bar arms 552 in the third ring 540c. The linkage connection pattern of the first two rings is therefore repeated. Although a straight link is used in this pattern, a non-linear link can also be used in this pattern without compromising the stent's profile.

Figure 13:
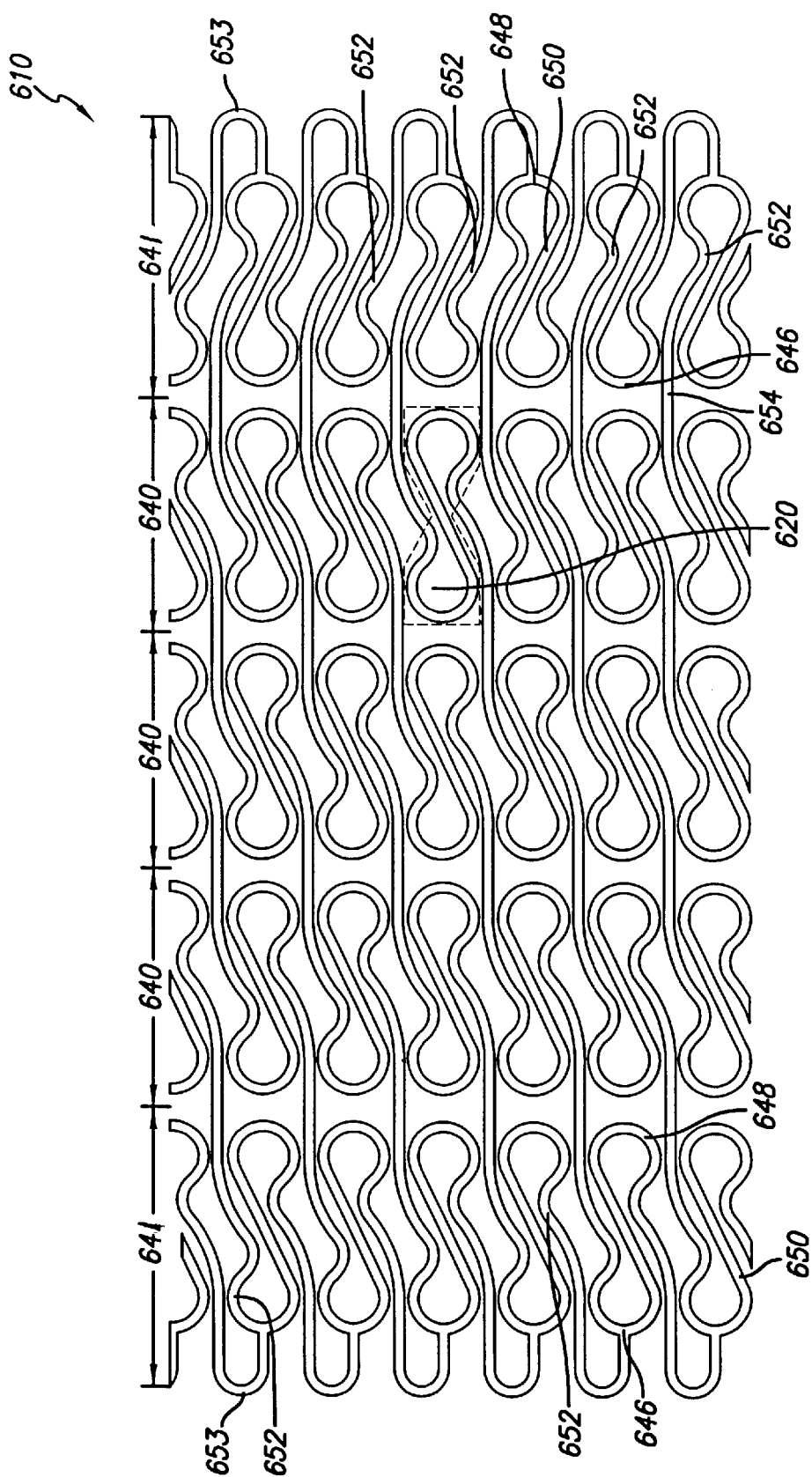
FIG. 13 is a plan view of another stent pattern with a body cell like a figure-eight comprised of one straight and two nonlinear bar arms.

FIG. 13 depicts yet another embodiment, stent pattern 610, with figure-eights 620. This is a 6-crown, 6-link design. FIG. 13 depicts an exemplary five-ring stent section. The figure-eight section of ring 640 uses one straight bar arm 650 and two non-linear bar arms 652, extending out from upper crests 646 and lower crests 648. The non-linear bar arms extend from the crests, and follow through with a single turn. These non-linear bar arms extend from the upper crest 646 of one ring 640 to the more distal lower crest 648 of the adjacent ring. Hence, the non-linear bar arms also act as connecting links 654 between adjacent rings. Due to this unique connection, the crests of the interior rings 640 are not connected circumferentially, but are connected longitudinally. As for the end rings 641, a similar non-linear bar arm 652 extends from the end crests 646, 648 and connects the body rings 640. In addition, a secondary non-linear bar arm 653 connects the crests 646, 648 nearest the body and follows through in a U-loop to form a connection with the head of the adjacent figure-eight element 620 in the same ring 641. The U-loop feature adds a greater expansion range and serves to connect the figure-eights to form a cylindrical structure. Hence, the crests 646, 648 of the end rings 640 are connected both circumferentially to one adjacent figure-eight element 620 in the same ring and longitudinally to another figure-eight element 620 in an adjacent ring. Although a straight link is used in this pattern, a non-linear link can also be used without compromising crimp profile.

Figure 14:
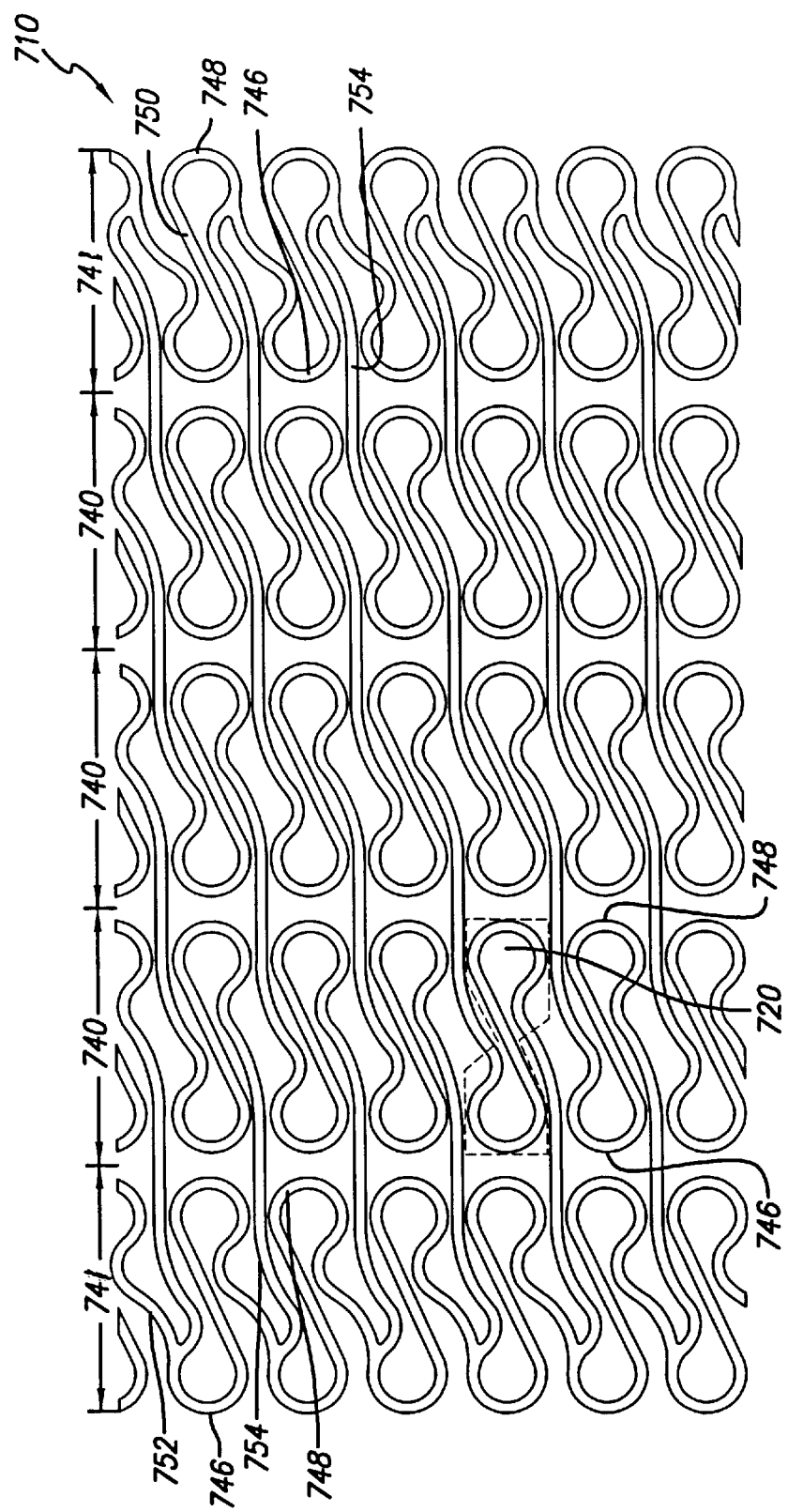
FIG. 14 is a plan view of another embodiment with one straight and two nonlinear bar arms.

Another embodiment, FIG. 14, is a 6-crown, 6-link partial stent pattern 710 with figure-eights 720. Like pattern 610, it is composed of one straight bar arm 750 and two non-linear bar arms 752 extending out from the upper and lower crests 646, 648 to form the figure-eight. Stent pattern 710 combines features of stent patterns 510 and 610. Pattern 710 uses the non-linear bar arms 752 to act as the links 754 between adjacent interior rings 740. Like stent pattern 510 however, the rings 741 at the end of stent 710 have their links 754 connected to an interior portion of the non-linear bar arm 752. Due to this unique configuration, the crests 746, 748 of the rings 741 in the interior of stent 710 are not connected circumferentially, but are connected longitudinally. Hence, the crests of the end rings 740 are connected both circumferentially to each other and longitudinally to the adjacent ring 740 of figure-eight elements. Although a straight link is used in this pattern, a non-linear link can also be used without compromising crimp profile.

Other embodiments of the invention, although not shown, are easily developed and fall within the scope of the present invention. One link may include more than one non-linear portion. For example, one could create a straight link with two differently shaped apertures. Alternatively, one could combine an undulating link with an aperture. Links are bar arms could have varying thickness.

The stent of the present invention can be made in many ways. One method of making the stent is to cut a thin-walled tubular member, such as stainless steel tubing, to remove portions of the tubing in the desired pattern for the stent, leaving relatively untouched the portions of the metallic tubing which are to form the stent. In accordance with the invention, it is preferred to cut the tubing in the desired pattern by means of a computer controlled laser equipment, as is well known in the art. Such methods are described in U.S. Pat. Nos. 5,759,192 and 5,780,807 to Saunders, which are incorporated herein by reference in their entirety.

The tubing may be made of suitable biocompatible material such as stainless steel or another metal alloy. The stainless steel tube may be alloy type: 316L SS, special chemistry per ASTM F138-92 or ASTM F139-92 grade 2. Special chemistry of type 316L per ASTM F138-92 or ASTM F139-92 stainless steel for surgical implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |

| | |
|---|---|
| -continued | |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The tubing is mounted in a rotatable collet fixture of a machine-controlled apparatus for positioning the tubing relative to a laser. According to machine-encoded instructions, the tubing is rotated and moved longitudinally relative to the laser, which is also machine controlled. The laser selectively removes the material from the tubing by ablation, thereby cutting a pattern into the tube.

The process of cutting a stent pattern into the tubing is automated, except for loading and unloading the length of tubing. In one example, a CNC opposing collet fixture for axial rotation of the length of tubing is used in conjunction with a CNC X/Y table to move the length of tubing axially relatively to a machine-controlled laser. The entire space between collets can be patterned using the $CO_2$ laser set-up of the foregoing example. The program for control of the apparatus is dependent on the particular configuration used and the pattern to be ablated in the coating.

Cutting a fine structure (e.g., a 0.0035 inch web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes for coronary stents are made typically of stainless steel with an outside diameter of 0.060 inch to 0.066 inch and a wall thickness of 0.002 inch to 0.004 inch. Dimensions for peripheral stents and other endoluminal prostheses may be different. These tubes are fixtured under a laser and positioned utilizing CNC equipment to generate a very intricate and precise pattern. Due to the thin wall and the small geometry of the stent pattern, it is necessary to have very precise control of the laser, its power level, the focused spot size, and the precise positioning of the laser cutting path.

Minimizing the heat input into the stent structure prevents thermal distortion, uncontrolled burn out of the metal, and metallurgical damage due to excessive heat, and thereby produces a smooth debris free cut. A Q-switched Nd-YAG, typically available from Quantronix of Hauppauge, N.Y., is utilized. The frequency is doubled to produce a green beam at 532 nanometers. Q-switching produces very short pulses (<100 nS) of high peak powers (kilowatts), low energy per pulse ($\leq 3$ mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up the stent structure. The system makes it possible to adjust the laser parameters to cut a narrow kerf width, which minimizes the heat input into the material.

The positioning of the tubular structure requires the use of precision CNC equipment, such as that manufactured and sold by Aerotech Corporation. In addition, a unique rotary mechanism has been provided that allows the computer program to be written as if the pattern were being cut from a flat sheet. This allows both circular and linear interpolation to be utilized in programming.

The optical system, which expands the original laser beam, delivers the beam through a viewing head and focuses the beam onto the surface of the tube. It incorporates a coaxial gas jet and nozzle that help to remove debris from the kerf and cool the region where the beam cuts and vaporizes the metal. It is also necessary to block the beam as it cuts through the top surface of the tube and prevent the beam, along with the molten metal and debris from the cut, from impinging on the opposite, inner surface of the tube.

In addition to the laser and the CNC positioning equipment, the optical delivery system includes: a beam expander to increase the laser beam diameter; a circular polarizer, typically in the form of a quarter wave plate, to eliminate polarization effects in metal cutting; provisions for a spatial filter; a binocular viewing head and focusing lens; and, a coaxial gas jet that provides for the introduction of a gas stream that surrounds the focused beam and is directed along the beam axis. The coaxial gas jet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.). The oxygen reacts with the metal to assist in the cutting process, similar to oxy-acetylene cutting. The focused laser beam acts as an ignition source and controls the reaction of the oxygen with the metal. In this manner, it is possible to cut the material with a very fine, precise kerf. In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris block protecting the far wall I.D.

Alternatively, burning may be prevented by inserting a second tube inside the stent tube. The second tube has an opening to trap the excess energy in the beam, which is transmitted through the kerf and which collects the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied, creating a small jet that would force the debris out of the laser cut kerf from the inside out. This would eliminate any debris from forming or collecting on the inside of the stent structure. It would place all the debris on the outside. With the use of special protective coatings, the resultant debris could be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005 inch) with the molten slag re-solidifying along the cut. This traps some scrap, thus requiring further processing. In order to remove the slag debris from the cut, it is necessary to soak the cut tube in a solution of HCL for approximately eight minutes at a temperature of approximately 55 ° C. Before it is soaked, the tube is placed in an alcohol and water bath and ultrasonically cleaned for approximately one minute. This removes the loose debris left from the cutting operation. After soaking, the tube is then ultrasonically cleaned in the heated HCL for one to four minutes, depending upon the wall thickness. To prevent cracking or breaking of the struts attached to the material left at the two ends of the stent pattern due to harmonic oscillations induced by the ultrasonic cleaner, a mandrel is placed down the center of the tube during the cleaning and scrap removal process. At the completion of this process, the stent structure is rinsed in water and is now ready for electropolishing.

The stents are preferably electrochemically polished in an acidic aqueous solution such as a solution of ELECTRO-GLO#300, sold by ELECTRO-GLO Co., Inc,. Chicago, Ill., which is a mixture of sulfuric acid, carboxylic acid, phosphates, corrosion inhibitors and a biodegradable surface active agent. The bath temperature is maintained at about 110°–135°F. and the current density is about 0.4 to about 1.5 amps per in.$^2$. Cathode to anode area should be at least about two to one. The stents may be further treated if desired, for example by applying a biocompatible coating.

It will be apparent that both focused laser spot size and depth of focus can be controlled by selecting beam diameter and focal length for the focusing lens. It will be apparent that increasing laser beam diameter, or reducing lens focal length, reduces spot size at the cost of depth of field.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal. The struts have generally perpendicular edges formed by the laser cut. The resulting stent structure provides superior performance.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to titanium, tantalum, nickel titanium and nickel/titanium/vanadium. Any of the superelastic or shape memory alloys can be formed into a tube and laser cut in order to form the pattern of the stent of the present invention. As is well known, the superelastic or shape memory alloys of the stent of the present invention can include the type known as thermoelastic martensitic transformation, or display stress-induced martensite. These types of alloys are well known in the art and need not be further described here.

Importantly, a stent formed of shape memory or superelastic alloys, whether the thermoelastic or the stress-induced martensite-type, can be delivered using a balloon catheter of the type described herein, or in the case of stress induced martensite, be delivered via a sheath catheter or a catheter without a balloon.

While the invention has been illustrated and described herein in terms of its use as an intravascular stent, it will be apparent to those skilled in the art that the stent can be used in other body lumens. Further, particular sizes and dimensions, the configuration of undulations, number of crowns per ring, materials used, and other features have been described herein and are provided as examples only. Other modifications and improvements may be made without departing from the scope of the invention. For example, the cylindrical rings can be octagonal, hexagonal, or some other polygon, thus possessing corners. Each ring is essentially a short tube, (or hoop or ring) whose length is preferably shorter than its diameter and which has a significant percentage of the tube surface removed. Other modifications could include the use of polymers in portions of the links and/or bar arms so that the stent would be more radiopaque. Alternatively, one could place electrical discontinuities in the stent to minimize the Faraday Cage effect and make the stent more visible under Magnetic Resonance Imaging.

What is claimed is:

1. An intravascular stent for use in a body lumen, comprising:
    a plurality of cylindrical rings aligned along a longitudinal axis, each ring having
        a first, delivery diameter,
        a second, implanted diameter,
        proximal and distal ends defining a generally cylindrical wall extending circumferentially between the proximal and distal ends,
        a plurality of figure-eights comprising open loops, the figure-eights being configured such that an open loop includes first and second loop ends diagonally opposed from first and second oppositely disposed loop ends of an oppositely disposed loop, the first loop end being diagonally connected by a straight bar to the second oppositely disposed loop end and the second loop end pointing toward the first oppositely disposed loop end;
    non-linear bar arms and straight bar arms, wherein the straight bar arms have a first arm axis and the nonlinear bar arms have a second arm axis, and wherein the non-linear bar arms include the open loops;
    at least one link having a first end and a second end, wherein the first link end is connected to an open loop of one ring and the second link end is connected to an open loop of an adjacent ring; and wherein the stent has a longitudinal axis parallel to the at least one link.

2. The stent of claim 1, wherein the first and second arm axes are parallel.

3. The stent of claim 1, wherein the first and second arm axes are at acute angles to each other.

4. The stent of claim 1, wherein the straight bar arms are adjacent to the non-linear bar arms.

5. The stent of claim 1, wherein the connecting links include a bounded aperture disposed between the cylindrical rings.

6. The stent of claim 5, wherein the aperture is an oval.

7. The stent of claim 5, wherein the aperture is generally rectangular.

8. The aperture of claim 5, wherein the aperture is generally in the shaper of a dog bone.

9. An expandable endovascular prosthesis comprising:
    a plurality of adjacent, expandable undulating rings, each ring comprising a plurality of figure eight shaped portions; each figure-eight shaped portion being formed by a straight intermediate bar arm connected to a portion of two non-linear bar arms to define a plurality of crests; and
    at least one link connecting each ring to an adjacent ring, the link being connected to the crest of one ring and to an intermediate portion of a bar arm of an adjacent ring.

10. The prosthesis of claim 9, wherein the two non-linear bar arms are sinusoidally shaped.

11. The prosthesis of claim 9, wherein the intermediate portion of the bar arm is the middle of the bar arm.

12. The prosthesis of claim 11, wherein the bar arm with the intermediate portion is a non linear bar arm.

13. The prosthesis of claim 12, wherein the prosthesis comprises repeating patterns of two adjacent rings.

* * * * *

UNITED STATES PATENT AND TRADEMARK OFFICE
CERTIFICATE OF CORRECTION

PATENT NO. : 6,749,629 B1 Page 1 of 1
DATED : June 15, 2004
INVENTOR(S) : James Hong, E. Tina Cheng and Stephen D. Ainsworth It is certified that error appears in the above-identified patent and that said Letters Patent is hereby corrected as shown below:

Title page
Item [56], References Cited, U.S. PATENT DOCUMENTS, delete "4,827,321" and insert -- 5,827,321 --.

Column 12,
Line 48, delete "shaper" and insert -- shape --.

Signed and Sealed this

Third Day of May, 2005

JON W. DUDAS
*Director of the United States Patent and Trademark Office*